United States Patent
Ikariya

Patent Number: 5,824,830
Date of Patent: Oct. 20, 1998

[54] RUTHENIUM-PHOSPHINE COMPLEX

[75] Inventor: Takao Ikariya, Tokyo, Japan

[73] Assignee: Takasago International Corporation, Tokyo, Japan

[21] Appl. No.: 909,938

[22] Filed: Aug. 12, 1997

[30] Foreign Application Priority Data

Aug. 15, 1996 [JP] Japan ................................ 8-232650

[51] Int. Cl.$^6$ .................................................. C07C 5/10
[52] U.S. Cl. ........................ 585/269; 585/273; 585/419
[58] Field of Search .................................. 585/269, 273, 585/419; 518/715

[56] References Cited

U.S. PATENT DOCUMENTS

| | | | |
|---|---|---|---|
| 4,994,602 | 2/1991 | Seido et al. | 560/186 |
| 5,360,908 | 11/1994 | Broger et al. | 546/146 |

FOREIGN PATENT DOCUMENTS

WO 95/18784  7/1995  WIPO ............................. C07C 67/31

OTHER PUBLICATIONS

Ohkuma et al., J. Org. Chem., 61:48–72–4873, 1996.

*Primary Examiner*—Scott W. Houtteman
*Attorney, Agent, or Firm*—Sughrue, Mion, Zinn, Macpeak & Seas, PLLC

[57] ABSTRACT

A novel ruthenium-phosphine complex useful as a catalyst for asymmetric hydrogenation is disclosed, which is represented by formula (I):

$${\rm \{RuCl(R\text{-}BINAP)\}\{Ru(EtNH_2)(R\text{-}BINAP)\}(\mu\text{-}Cl)_3} \qquad (I)$$

wherein Et stands for an ethyl group; and R-BINAP represents a tertiary phosphine represented by formula (II):

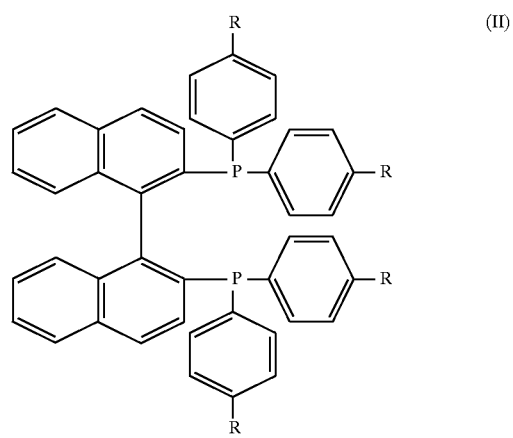

wherein R represents a hydrogen atom or a methyl group.

2 Claims, 1 Drawing Sheet

RUTHENIUM-PHOSPHINE COMPLEX

FIELD OF THE INVENTION

This invention relates to a novel ruthenium-phosphine complex.

FIELD OF THE INVENTION

Numerous organic synthesis reactions using a transition metal complex as a catalyst have been developed and utilized for diverse purposes. In particular, various asymmetric catalysts for asymmetric hydrogenation have been reported. Ever since the report on synthesis of an asymmetric hydrogenation product having a high optical purity by asymmetric hydrogenation using a complex made up of a rhodium atom and an optically active phosphine as a ligand, there has been a large number of reports made on asymmetric hydrogenation using a complex formed of a transition metal atom and an optically active phosphine as a catalyst for asymmetric hydrogenation.

For example, *J. Chem. Soc., Chem. Commun.*, p. 922 (1985) and *J. Chem. Soc. Perkin Trans. I*, p. 1571 (1987) teach a technique for preparing an optically active amino acid derivative by hydrogenating an acylaminoacrylic acid derivative using a 2,2-bis(diphenylphosphino)-1,1'-binaphthylruthenium complex (hereinafter referred to as a BINAP-Ru complex).

SUMMARY OF THE INVENTION

As a result of study on the synthesis and structure of BINAP-Ru complex, the inventors of the present invention have found a novel compound having a ruthenium atom to which BINAP, a chlorine atom, and EtNH$_2$ (Et: ethyl) are coordinated. They have obtained a single crystal of the compound by recrystallization and identified its structure through X-ray crystal structure analysis, etc. As a result of further investigation, this novel compound has been proved useful as a catalyst for asymmetric reactions. The present invention has been completed based on this finding.

The present invention provides a ruthenium-phosphine complex represented by formula (I):

$$\{RuCl(R\text{-}BINAP)\}\{Ru(EtNH_2)(R\text{-}BINAP)\}(\mu\text{-}Cl)_3 \quad (I)$$

wherein Et stands for an ethyl group; and R-BINAP represents a tertiary phosphine represented by formula (II):

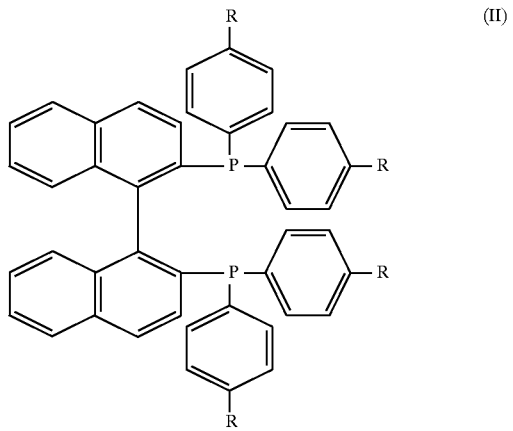

wherein R represents a hydrogen atom or a methyl group.

The present invention also provides an optically active ruthenium-phosphine complex represented by formula (III):

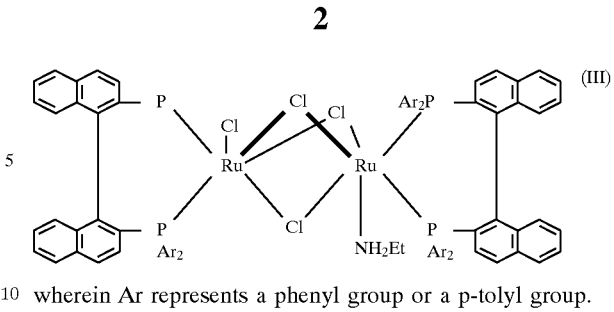

wherein Ar represents a phenyl group or a p-tolyl group.

DETAILED DESCRIPTION OF THE INVENTION

Figure 1:
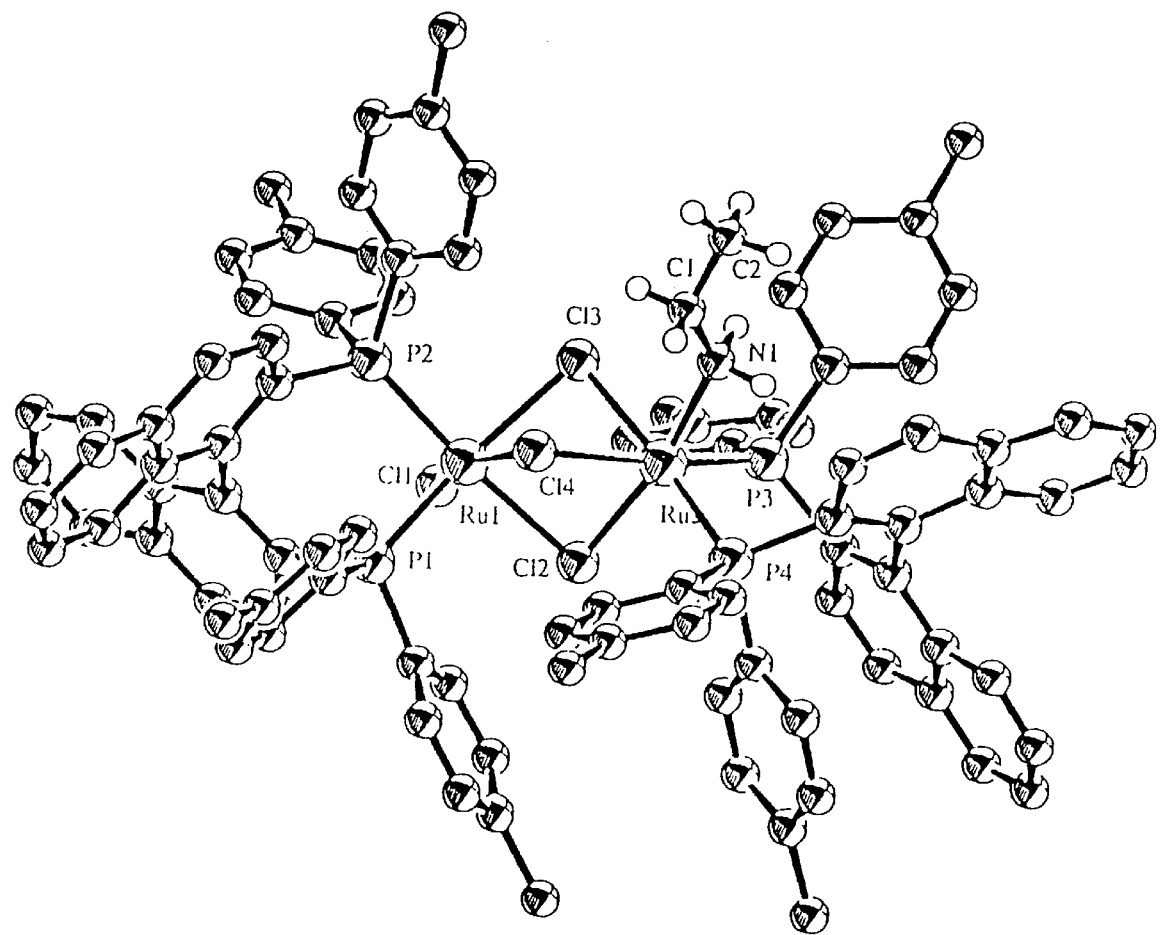
FIG. 1 is an ORTEP image of the ruthenium-phosphine complex obtained in Example 1.

The complex according to the present invention can be prepared by reacting R-BINAP and a ruthenium compound represented by formula [Ru(cod)Cl$_2$]$_n$ (wherein cod represents 1,5-cyclooctadiene) in a solvent such as benzene, toluene and xylene in the presence of a base such as triethylamine. R-BINAP used here is synthesized by the process disclosed in Takaya, et al., *J. Org. Chem.*, Vol. 51, p. 629 (1986). [Ru(cod)Cl$_2$]$_n$ is synthesized by the process described in M. A. Bennet et al., *Chem. Ind.*, p. 1516 (1959).

The reaction is carried out at a temperature of 80° to 150° C., preferably 100° to 140° C., more preferably 110° to 130° C., for 6 to 12 hours, preferably 7 to 9 hours. The base to be used includes triethylamine. The solvent to be used preferably includes toluene and xylene. After the reaction, the solvent is evaporated, and the residue is recrystallized from toluene and hexane to obtain the complex of the invention as clear deep red crystals.

The structure of the complex was established as follows.

The crystals of (I) suitable for X-ray diffraction studies were sealed in glass capillaries under argon atmosphere, and then a crystal was mounted on a Rigaku AFC-7R four-circle diffractometer for data collection using CuKα radiation. The unit cell parameters at 20° C. were determined by a least-squares fit to 2θ values of 25 strong higher reflections for all complexes. Three standard reflections were chosen and monitored every 150 reflections. Absorption correction was not carried out due to small $\mu$ value. Every sample showed no significant intensity decay during the data collection. The crystal structures were solved by the direct method (SAPI90) and refined by the full-matrix least squares method.

All calculations were performed using the TEXSAN crystallographic software package, and illustrations were drawn with ORTEP.

The complex of the present invention can be used for asymmetric hydrogenation of a β-keto ester either as a single compound or a complex mixture obtained as a reaction product. The asymmetric hydrogenation reaction can be conducted by stirring a β-keto ester, such as methyl acetoacetate, ethyl acetoacetate or ethyl 4-chloroacetoacetate, and the complex of the present invention and/or the reaction product in a solvent in a hydrogen atmosphere.

In the asymmetric hydrogenation reaction, it is preferable for better results that the P-keto ester be used in an amount of 1000 to 10000 mol per mol of the complex. The reaction temperature preferably ranges from 10° to 50° C. The solvent for hydrogenation preferably includes methanol, ethanol, and a mixed solvent of such an alcohol and methylene chloride.

The hydrogenation product obtained by the asymmetric hydrogenation can arbitrarily be an R-form or an S-form depending on the choice from the R-form and S-form of R-BINAP. The hydrogenation product having an optical purity of 95% e.e. or higher can be obtained with ease.

As described above, the novel ruthenium-phosphine complex of the present invention is useful as a catalyst for asymmetric hydrogenation. Asymmetric hydrogenation of a β-keto ester using the complex of-the invention as a catalyst gives an optically active hydrogenation product at a high optical purity easily and efficiently.

The present invention will now be illustrated in greater detail with reference to Examples, but it should be understood that the present invention is not limited thereto. Unless otherwise indicated, all the percents are by weight.

In Examples, measurements of physical properties were made with the following equipment.

Gas-liquid chromatography: GC-15A manufactured by Shimadzu Corp.

High-performance liquid chromatography (HPLC): LC-4A manufactured by Shimadzu Corp.

Melting point: MP-500D manufactured by Yanagimoto Seisakusho K.K.

Elementary analysis: YANAKO MT-5CHN CORDER manufactured by Yanagimoto Seisakusho K.K.

X-Ray analysis: AFC-7R manufactured by Rigaku K.K.

EXAMPLE 1

(R)-2,2'-Bis[di(p-tolyl)phosphino]-1,1'-binaphthyl (202 mg, 0.27 mmol), 76 mg (0.27 mmol) of $[Ru(cod)Cl_2]_n$, 30 ml of toluene, and 0.2 ml of triethylamine were heated at 110° C. for 58 hours while stirring. After completion of the reaction, the reaction solution was concentrated, and the residue was recrystallized from 10 ml of toluene and 5 ml of hexane to give 97 mg (83%) of deep red crystals.

Melting point: 120° C. (decomposition);

Elementary analysis for $C_{98}H_{87}Cl_4NP_4Ru_2(C_6H_5CH_3)_2$; Calcd. (%): C, 69.67; H, 5.38; N, 0.72; Found (%): C, 69.09; H, 5.15; N, 0.71.

The resulting complex contained two molecules of toluene.

The crystal was sealed in glass capillaries under argon atmosphere, and then a crystal was mounted on a Rigaku AFC-7R four-circle diffractometer for data collection using CuKα radiation. Measured non-equivalent reflections with I>3.0σ(I) were used for the structure determination. In the subsequent refinement the function $\Sigma\omega(|Fo|-|Fc|)^2$ was minimized, where $|Fo|$ and $|Rc|$ are the observed and calculated structure factors amplitudes, respectively. The agreement indices are defined as $R=\Sigma||Fo|-|Fc||/\Sigma|Fo|$ and $R\omega=[\Sigma\omega(|Fo|-|Fc|)^2/\Sigma\omega(|Fo|)^2]^{1/2}$ where $\omega^{-1}=\sigma^2(Fo)=\sigma^2(Fo^2)/(4Fo^2)$. The positions of all non-hydrogen atoms for all complexes were found from a difference Fourier electron density map and refined anisotropically. Hydrogen atoms bound to aromatic carbon atoms were located as fixed contributions after idealization (C—H=0.95 Å). All calculations were performed using the TEXSAN crystallographic software package, and illustrations were drawn with ORTEP. The ORTEP image depicted based on these data are shown in FIG. 1.

Measurement Data and Data Concerning Analytical Results:

Molecular formula: $C_{112}H_{103}Cl_4NP_4Ru_2$

Molecular weight: 1930.9

Crystal system: orthorhombic

Space group: $P2_12_12_1$ a: 17.908 Å (3)

b: 47.841 Å (8)

c: 11.324 Å (5)

Z (number of molecules per unit cell): 4

V (volume of unit cell): 9701 Å³ (4)

Dcalcd. (calculated density): 1.32 g/cm³

F(000) (number of electrons per unit cell): 4580

Radiation: CuKα

Crystal size: 0.1×0.1×0.1 mm

Linear absorption coefficient: 45.98 m$^{-1}$

Scan mode: ω–2θ

Temperature: 20° C.

Scan speed: 16°/min

Scan width: 0.79°+0.20 tan θ

2θmax: 120.2°

Unique data (observed): 8029

Unique date (I>3σ(I)): 5351

No. of variables: 1091

R (R factor): 0.049

Rω: 0.057

Δ: 0.53 eÅ$^{-3}$, 0.51 eÅ$^{-3}$ xyz Coordinates:

| atom | x | | y | | z | | βeq (equivalent temperature factor) |
|------|-----|-----|-----|-----|-----|-----|-----|
| Ru(1) | 0.13097 | (6) | 0.11012 | (2) | 0.18313 | (10) | 2.47 (2) |
| Ru(2) | 0.00883 | (6) | 0.09617 | (2) | 0.39707 | (10) | 2.50 (2) |
| Cl(1) | 0.0953 | (2) | 0.09261 | (7) | -0.0066 | (3) | 3.38 (8) |
| Cl(2) | -0.0040 | (2) | 0.11903 | (6) | 0.2115 | (3) | 3.06 (8) |
| Cl(3) | 0.0970 | (2) | 0.06498 | (7) | 0.2877 | (3) | 2.97 (8) |
| Cl(4) | 0.1282 | (2) | 0.12415 | (7) | 0.3922 | (3) | 3.08 (7) |
| P(1) | 0.1507 | (2) | 0.15186 | (7) | 0.0956 | (3) | 2.59 (8) |
| P(2) | 0.2508 | (2) | 0.9627 | (8) | 0.1584 | (3) | 3.07 (8) |
| P(3) | -0.0871 | (2) | 0.06561 | (7) | 0.3767 | (3) | 2.85 (8) |
| P(4) | -0.0649 | (2) | 0.12711 | (7) | 0.4926 | (3) | 2.71 (8) |
| N(1) | 0.0439 | (7) | 0.0759 | (2) | 0.555 | (1) | 3.9 (3) |
| C(1) | 0.107 | (1) | 0.0763 | (5) | 0.613 | (2) | 8.4 (7) |
| C(2) | 0.127 | (1) | 0.0589 | (5) | 0.714 | (2) | 7.9 (6) |
| C(3) | 0.0624 | (8) | 0.1704 | (3) | 0.065 | (1) | 2.5 (3) |
| C(4) | 0.0062 | (8) | 0.1575 | (3) | 0.000 | (1) | 2.8 (3) |
| C(5) | -0.0641 | (9) | 0.1698 | (3) | -0.011 | (1) | 3.7 (4) |
| C(6) | -0.0770 | (9) | 0.1953 | (4) | 0.037 | (2) | 4.4 (4) |
| C(7) | -0.021 | (1) | 0.2085 | (3) | 0.102 | (2) | 5.4 (5) |
| C(8) | 0.0461 | (9) | 0.1965 | (3) | 0.116 | (2) | 4.0 (4) |
| C(9) | -0.156 | (1) | 0.2094 | (4) | 0.021 | (2) | 7.3 (6) |
| C(10) | 0.2030 | (8) | 0.1803 | (3) | 0.163 | (1) | 3.0 (3) |
| C(11) | 0.2177 | (8) | 0.2046 | (3) | 0.100 | (1) | 3.3 (3) |
| C(12) | 0.254 | (1) | 0.2257 | (4) | 0.147 | (2) | 5.3 (5) |
| C(13) | 0.279 | (1) | 0.2254 | (3) | 0.267 | (2) | 5.1 (5) |
| C(14) | 0.263 | (1) | 0.2018 | (4) | 0.330 | (2) | 5.6 (5) |
| C(15) | 0.2253 | (9) | 0.1785 | (3) | 0.283 | (1) | 3.8 (4) |
| C(16) | 0.323 | (1) | 0.2494 | (5) | 0.321 | (2) | 8.9 (8) |
| C(17) | 0.1955 | (8) | 0.1486 | (3) | -0.049 | (1) | 2.4 (3) |
| C(18) | 0.1529 | (8) | 0.1512 | (3) | -0.152 | (1) | 3.3 (4) |
| C(19) | 0.1843 | (9) | 0.1457 | (3) | -0.258 | (2) | 4.1 (4) |
| C(20) | 0.258 | (1) | 0.1374 | (3) | -0.272 | (1) | 4.2 (4) |
| C(21) | 0.290 | (1) | 0.1311 | (4) | -0.386 | (2) | 4.9 (5) |

-continued xyz Coordinates:

| atom | x | y | z | βeq (equivalent temperature factor) |
|---|---|---|---|---|
| C(22) | 0.363 (1) | 0.1242 (4) | −0.392 (2) | 5.2 (5) |
| C(23) | 0.4094 (10) | 0.1231 (4) | −0.291 (2) | 5.2 (5) |
| C(24) | 0.3814 (9) | 0.1294 (3) | −0.181 (2) | 4.4 (4) |
| C(25) | 0.3028 (8) | 0.1361 (3) | −0.167 (1) | 3.5 (4) |
| C(26) | 0.2710 (9) | 0.1421 (3) | −0.057 (1) | 2.7 (3) |
| C(27) | 0.3221 (7) | 0.1247 (3) | 0.139 (1) | 2.8 (3) |
| C(28) | 0.368 (1) | 0.1297 (4) | 0.237 (2) | 5.4 (5) |
| C(29) | 0.415 (1) | 0.1521 (4) | 0.244 (2) | 6.1 (5) |
| C(30) | 0.4163 (9) | 0.1718 (3) | 0.152 (2) | 4.2 (4) |
| C(31) | 0.4617 (9) | 0.1969 (4) | 0.160 (2) | 5.3 (5) |
| C(32) | 0.464 (1) | 0.2158 (4) | 0.070 (2) | 6.4 (6) |
| C(33) | 0.4165 (9) | 0.2102 (4) | −0.029 (2) | 4.8 (5) |
| C(34) | 0.3725 (9) | 0.1876 (3) | −0.038 (1) | 3.9 (4) |
| C(35) | 0.3700 (8) | 0.1674 (3) | 0.052 (1) | 3.5 (4) |
| C(36) | 0.3207 (7) | 0.1434 (3) | 0.048 (1) | 2.8 (3) |
| C(37) | 0.2668 (9) | 0.0714 (3) | 0.037 (1) | 3.3 (4) |
| C(38) | 0.3270 (9) | 0.0720 (3) | −0.039 (1) | 4.0 (4) |
| C(39) | 0.342 (1) | 0.0504 (4) | −0.113 (2) | 6.0 (5) |
| C(40) | 0.295 (1) | 0.0270 (4) | −0.113 (2) | 5.5 (5) |
| C(41) | 0.234 (1) | 0.0261 (3) | −0.040 (1) | 4.7 (4) |
| C(42) | 0.2190 (10) | 0.0477 (3) | 0.036 (1) | 4.3 (4) |
| C(43) | 0.311 (1) | 0.0023 (4) | −0.200 (2) | 8.1 (7) |
| C(44) | 0.2962 (8) | 0.0750 (3) | 0.277 (1) | 3.3 (4) |
| C(45) | 0.354 (1) | 0.0585 (5) | 0.249 (2) | 8.7 (7) |
| C(46) | 0.394 (1) | 0.0441 (5) | 0.336 (2) | 9.5 (8) |
| C(47) | 0.376 (1) | 0.0473 (4) | 0.455 (2) | 5.4 (5) |
| C(48) | 0.3137 (10) | 0.0622 (4) | 0.478 (2) | 4.8 (5) |
| C(49) | 0.2733 (9) | 0.0763 (3) | 0.392 (2) | 3.8 (4) |
| C(50) | 0.420 (1) | 0.0324 (5) | 0.549 (2) | 9.5 (8) |
| C(51) | −0.0907 (8) | 0.0459 (3) | 0.238 (1) | 3.2 (4) |
| C(52) | −0.0491 (9) | 0.0519 (3) | 0.138 (1) | 4.0 (4) |
| C(53) | −0.0506 (10) | 0.0356 (3) | 0.037 (1) | 4.5 (4) |
| C(54) | −0.1012 (10) | 0.0130 (4) | 0.030 (2) | 4.6 (5) |
| C(55) | −0.146 (1) | 0.0065 (3) | 0.126 (1) | 5.4 (5) |
| C(56) | −0.140 (1) | 0.0229 (3) | 0.230 (1) | 4.3 (4) |
| C(57) | −0.108 (1) | −0.0040 (4) | −0.084 (2) | 6.9 (6) |
| C(58) | −0.0813 (9) | 0.0344 (3) | 0.472 (1) | 3.3 (4) |
| C(59) | −0.0159 (9) | 0.0183 (3) | 0.462 (1) | 5.0 (5) |
| C(60) | −0.0121 (10) | −0.0070 (3) | 0.518 (2) | 5.2 (5) |
| C(61) | −0.0694 (9) | −0.0177 (3) | 0.586 (1) | 4.2 (4) |
| C(62) | −0.1326 (9) | −0.0014 (3) | 0.593 (1) | 4.0 (4) |
| C(63) | −0.1402 (9) | 0.0242 (3) | 0.542 (1) | 3.4 (4) |
| C(64) | −0.064 (1) | −0.0466 (3) | 0.637 (2) | 6.1 (5) |
| C(65) | −0.1836 (7) | 0.0791 (3) | 0.392 (1) | 2.5 (3) |
| C(66) | −0.2270 (9) | 0.0794 (3) | 0.288 (1) | 3.9 (4) |
| C(67) | −0.2978 (9) | 0.0905 (3) | 0.286 (1) | 3.9 (4) |
| C(68) | −0.3285 (8) | 0.1032 (3) | 0.384 (2) | 4.0 (4) |
| C(69) | −0.400 (1) | 0.1150 (3) | 0.379 (2) | 5.6 (5) |
| C(70) | −0.4280 (9) | 0.1272 (4) | 0.471 (2) | 6.4 (6) |
| C(71) | −0.3862 (9) | 0.1300 (3) | 0.579 (2) | 5.3 (5) |
| C(72) | −0.3181 (8) | 0.1186 (3) | 0.587 (2) | 4.5 (4) |
| C(73) | −0.2862 (7) | 0.1041 (3) | 0.489 (1) | 3.2 (4) |
| C(74) | −0.2133 (8) | 0.0912 (3) | 0.492 (1) | 3.8 (4) |
| C(75) | −0.1055 (7) | 0.1091 (3) | 0.619 (1) | 2.9 (3) |
| C(76) | −0.0671 (7) | 0.1079 (3) | 0.731 (1) | 2.9 (3) |
| C(77) | −0.0925 (8) | 0.0951 (3) | 0.828 (1) | 3.7 (4) |
| C(78) | −0.1616 (8) | 0.0816 (3) | 0.823 (1) | 3.5 (4) |
| C(79) | −0.1956 (10) | 0.0696 (4) | 0.925 (1) | 4.5 (5) |
| C(80) | −0.262 (1) | 0.0547 (4) | 0.915 (2) | 5.1 (5) |
| C(81) | −0.2963 (10) | 0.0514 (3) | 0.810 (2) | 4.6 (4) |
| C(82) | −0.2677 (9) | 0.0627 (3) | 0.708 (1) | 3.9 (4) |
| C(83) | −0.2018 (7) | 0.0788 (3) | 0.713 (1) | 2.9 (3) |
| C(84) | −0.1721 (7) | 0.0926 (3) | 0.609 (1) | 3.1 (3) |
| C(85) | −0.1453 (9) | 0.1456 (3) | 0.425 (1) | 3.4 (4) |
| C(86) | −0.191 (1) | 0.1639 (3) | 0.492 (2) | 4.9 (5) |
| C(87) | −0.250 (1) | 0.1774 (4) | 0.441 (2) | 5.7 (6) |
| C(88) | −0.2674 (10) | 0.1751 (4) | 0.325 (2) | 5.5 (5) |
| C(89) | −0.2243 (10) | 0.1573 (4) | 0.255 (2) | 5.1 (5) |
| C(90) | −0.1640 (8) | 0.1436 (3) | 0.304 (2) | 4.1 (4) |
| C(91) | −0.336 (1) | 0.1897 (5) | 0.273 (2) | 8.6 (7) |
| C(92) | −0.0183 (8) | 0.1589 (3) | 0.552 (1) | 2.7 (3) |
| C(93) | 0.0262 (9) | 0.1737 (3) | 0.473 (2) | 4.1 (4) |
| C(94) | 0.061 (1) | 0.1986 (4) | 0.512 (2) | 6.4 (6) |
| C(95) | 0.047 (1) | 0.2088 (4) | 0.622 (2) | 6.0 (6) |
| C(96) | 0.001 (1) | 0.1950 (3) | 0.703 (2) | 6.0 (5) |
| C(97) | −0.0304 (10) | 0.1707 (3) | 0.665 (2) | 4.6 (4) |
| C(98) | 0.085 (1) | 0.2357 (5) | 0.664 (3) | 11 (1) |

APPLICATION EXAMPLE 1

Hydrogenation of Methyl Acetoacetate

Methyl acetoacetate (0.70 g, 6.0 mmol) and 3.1 mg (1.5 μmol) of the complex obtained in Example 1 were stirred in a mixture of 3 ml of methanol and 1 ml of methylene chloride at 30° C. under a hydrogen pressure of 100 atm for 27 hours. After confirming the completion of the reaction by gas chromatography, the solvent was removed by evaporation to obtain 0.68 g of methyl 3-hydroxybutyrate.

The resulting methyl 3-hydroxybutyrate was reacted with (R)-(+)-α-methoxy-α-trifluoromethylphenylacetic acid chloride to synthesize methyl 3-[((R)-(+)-α-methoxy-α-trifluoromethylphenylacetoxy]butyrate. The product was subjected to HPLC (column: A-003-3 SIL (⌀4.6×250 mm), manufactured by YMC; eluent: hexane/ethyl ether=8/2 by volume; flow rate: 1 ml/min; detection: UV 250 nm) to separate diastereomers. As a result of analysis, the starting alcohol was found to be a mixture of 99.5% of methyl (R)-(−)-3-hydroxybutyrate and 0.5% of methyl (S)-(+)-3-hydroxybutyrate. Accordingly, the enantiomer excess was 99% e.e.

While the invention has been described in detail and with reference to specific examples thereof, it will be apparent to one skilled in the art that various changes and modifications can be made therein without departing from the spirit and scope thereof.

What is claimed is:

1. A ruthenium-phosphine complex represented by formula (I):

$$\{RuCl(R\text{-}BINAP)\}\{Ru(EtNH_2)\ (R\text{-}BINAP)\}(\mu\text{-}Cl)_3 \qquad (I)$$

wherein Et represents an ethyl group; and R-BINAP represents a tertiary phosphine represented by formula (II):

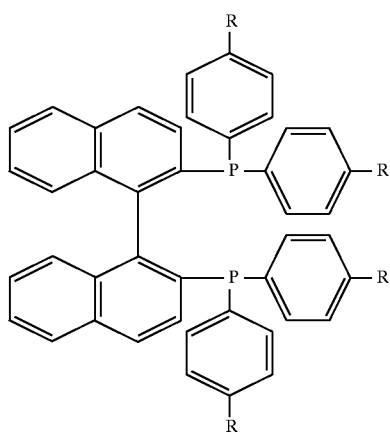
(II)
wherein R represents a hydrogen atom or a methyl group.
2. An optically active ruthenium-phosphine complex represented by formula (III):
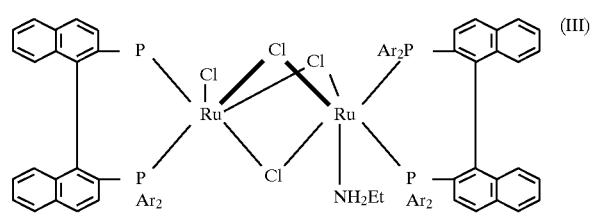
wherein Ar represents a phenyl group or a p-tolyl group.
* * * * *